(12) United States Patent
Kool

(10) Patent No.: US 7,749,699 B2
(45) Date of Patent: Jul. 6, 2010

(54) DETECTION OF CHEMICAL LIGATION USING FLUORESCENCE QUENCHING LEAVING GROUPS

(75) Inventor: Eric T. Kool, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 923 days.

(21) Appl. No.: 10/604,400

(22) Filed: Jul. 17, 2003

(65) Prior Publication Data

US 2004/0259102 A1 Dec. 23, 2004

Related U.S. Application Data

(60) Provisional application No. 60/396,774, filed on Jul. 18, 2002.

(51) Int. Cl.
*C12Q 1/68* (2006.01)
*C07H 21/02* (2006.01)
*C07H 21/04* (2006.01)
*C12P 19/34* (2006.01)

(52) U.S. Cl. .......................... 435/6; 536/23.1; 536/24.3

(58) Field of Classification Search ........................ None
See application file for complete search history.

(56) References Cited

U.S. PATENT DOCUMENTS

| 5,476,925 | A |  | 12/1995 | Letsinger et al. ............ 536/23.1 |
| 5,476,930 | A |  | 12/1995 | Letsinger et al. ............ 536/25.3 |
| 5,646,260 | A |  | 7/1997 | Letsinger et al. ............ 536/23.1 |
| 5,648,480 | A |  | 7/1997 | Letsinger et al. ........... 536/25.34 |
| 5,681,943 | A |  | 10/1997 | Letsinger et al. ........... 536/25.33 |
| 5,691,146 | A | * | 11/1997 | Mayrand ........................ 435/6 |
| 5,925,517 | A | * | 7/1999 | Tyagi et al. ..................... 435/6 |
| 5,932,718 | A |  | 8/1999 | Letsinger et al. ........... 536/25.33 |
| 5,952,202 | A | * | 9/1999 | Aoyagi et al. ................. 435/91.2 |
| 6,348,596 | B1 | * | 2/2002 | Lee et al. ........................ 546/75 |

OTHER PUBLICATIONS

Xu, Y. et al., "Nonenzymatic autoligation in direct three-color detection of RNA and DNA point mutations", Nature Biotech., vol. 19, pp. 148-152 (Feb. 2001).*
Stratagene Catalog, p. 39 (1988).*
Seitz, O., "Solid-Phase Synthesis of Doubly Labeled Peptide Nucleic Acids as Probes for the Real-time Detection of Hybridization", Angew. Chem. Int. Ed., vol. 39, pp. 3249-3252 (2000).*
"*Nucleophilic Reactions of Some Nucleoside Phosphorothioates*;" Stanislav Chladek and Joseph Nagyvary; J.. Am. Chem. Soc.; vol. 94, No. 6, Mar. 22, 1972; pp. 2079-2085.
"*Nucleoside S-Alkyl Phosphorothioates. IV. Synthesis of Nucleoside Phosphorotioate Monoesters*;" Alan F. Cook; J. Am. Chem. Soc.; vol. 92, No. 1; Jan. 14, 1970; pp. 190-195.
"*Multicolor Molecular Beacons for Allele Discrimination*;" Sanjay Tyagi, Diana P. Bratu and Fred Russell Kramer; Nature Biotechnology, vol. 16, Jan. 1998; pp. 49-53.
"*Enhancement of Selectivity in Recognition of Nucleic Acids Via Chemical Autoligation*;" Sergei M. Gryaznov; Ronald Schultz; Surendra K. Chaturvedi and Robert L. Letsinger; Nucleic Acids Research, vol. 22, No. 12, Jun. 25, 1994 Oxford University Press; pp. 2366-2369.
"*A Covalent Lock for Self-Assembled Oligonucleotide Conjugates*;" Mathis K. Herrlein, Jeffrey S. Nelson and Robert L. Letsinger; J. Am. Chem. Soc.; vol. 117, No. 40, Oct. 11, 1995; pp. 10151-10152.
"*A Novel 5'-Iodonucleoside Allows Efficient Nonenzymatic Ligation of Single-stranded and Duples DNAs*;" Yanzheng Xu and Eric T. Kool; Tetrahedron Letters, vol. 38, No. 32, Aug. 11, 1997; pp. 5595-5598.
"*Quencher as Leaving Group: Efficient Detection of DNA-Joining Reactions*;" Shinsuke Sando and Eric T. Kool; J. Am. Chem. Soc., vol. 124, No. 10, 2002; pp. 2096-2097.
"*Oligonucleotides with Fluorescent Dyes at Opposite Ends Provide a Quenched Probe System Useful for Detecting PCR Product and Nucleic Acid Hybridization*;" Kenneth J. Livak, Susan J.A. Flood, Jeffrey Marmaro, William Giusti, and Karin Deetz; PCR Methods and Applications, vol. 4, No. 6, Jun. 1995; pp. 357-362.
"*Imaging of RNA in Bacteria with Self-Ligating Quenched Probes*;" Shinsuke Sando and Eric T. Kool; J. Am. Chem. Soc., vol. 124, 2002; pp. 9686-9687.
"*Flow Cytometric Detection of Specific RNAs in Native Human Cells with Quenched Autoligating FRET Probes*;" Hiroshi Abe and Eric Kool; PNAS, vol. 103, No. 2, 2006; pp. 263-268.

* cited by examiner

Primary Examiner—Teresa E Strzelecka
(74) *Attorney, Agent, or Firm*—Howrey LLP

(57) ABSTRACT

Novel compounds having a fluorescence quencher as a leaving group are disclosed. Nucleic acids and other molecules containing a fluorophore and a fluorescence quencher are disclosed as an embodiment of this invention. The use of the oligonucleotides in enzyme-free oligonucleotide ligation reactions results in an increase in fluorescence when the oligonucleotide also contains a nearby fluorophore. The ligation reactions can be performed in solution, on surfaces, or in cells.

47 Claims, 3 Drawing Sheets

SEQUENCE LISTING

```
<160> NUMBER OF SEQ ID NOS: 6

<210> SEQ ID NO 1
<211> LENGTH: 13
<212> TYPE: DNA
<213> ORGANISM: Homo sapiens
<220> FEATURE:
<221> NAME/KEY: misc_feature
<222> LOCATION: (3)..(3)
<223> OTHER INFORMATION: fluorescein C-5-alkenyl conjugate of dU

<400> SEQUENCE: 1 tgnggggcaag agt                                                         13

<210> SEQ ID NO 2
<211> LENGTH: 50
<212> TYPE: DNA
<213> ORGANISM: Homo sapiens

<400> SEQUENCE: 2
atattcgacc accaccaccc gcggccgcca cacccgttct cacgcgactg                  50

<210> SEQ ID NO 3
<211> LENGTH: 50
<212> TYPE: DNA
<213> ORGANISM: Homo sapiens

<400> SEQUENCE: 3
atattcgacc accaccaccc gcggcagcca cacccgttct cacgcgactg                  50

<210> SEQ ID NO 4
<211> LENGTH: 7
<212> TYPE: DNA
<213> ORGANISM: Homo sapiens

<400> SEQUENCE: 4 ccgtcgg                                                                  7

<210> SEQ ID NO 5
<211> LENGTH: 5
<212> TYPE: DNA
<213> ORGANISM: Escherichia coli

<400> SEQUENCE: 5 gcaac                                                                    5

<210> SEQ ID NO 6
<211> LENGTH: 5
<212> TYPE: DNA
<213> ORGANISM: Escherichia coli

<400> SEQUENCE: 6 gccac                                                                    5
```

DETECTION OF CHEMICAL LIGATION USING FLUORESCENCE QUENCHING LEAVING GROUPS

CROSS REFERENCE TO RELATED APPLICATIONS

The present application claims priority to U.S. Provisional Patent Application Ser. No. 60/396,774 filed Jul. 18, 2002, the contents of which are incorporated herein by reference.

FEDERAL RESEARCH STATEMENT

The U.S. government may own rights in the present invention pursuant to grant number GM62658 from the U.S. National Institutes of Health and grant number DAAD19-00-1-0363-P00001 from the U.S. Army Research Office.

BACKGROUND OF INVENTION

1. Field of the Invention

The invention relates to methods of detecting chemical ligation. One example application involves methods of detecting nucleic acids and, more specifically, to methods for the detection of ligation of nucleic acids via a change in fluorescence properties. Methods for the detection of ligation by the use of a quencher as a leaving group are disclosed.

2. Description of the Related Art

As the molecular nature of diseases is studied, there is an increasing need for methods of detecting and analyzing nucleic acids both in vitro and in vivo. Recent work on sequencing the human genome has resulted in a flood of genomic and proteomic information. This information has made a significant and sometimes life-determining difference in the diagnosis, prognosis, and treatment of disease. In order to fully take advantage of this information, more quick and simple, yet accurate, methods of detecting and analyzing the presence or absence of nucleic acids, which may differ by as little as one nucleotide from others, need to be developed. In certain cases, the nucleic acids may be present in minute quantities or concentrations, which underscores the need for high sensitivity as well.

For example, drug resistance in bacterial infections is typically characterized genetically. Methods for characterizing infections commonly involve first culturing the organism, which takes days at least and months at worst. A specific example is the standard diagnosis of tuberculosis, which commonly takes several weeks, as the *Mycobacterium tuberculosis* organism is slow growing, and determination of antibiotic resistance takes more time still. Even short (e.g. two days) bacterial cultures are dangerously long for patients with other acute infections such as those occurring in sepsis or in necrotizing fasciitis. Thus, methods for genetic analysis are increasingly important and faster methods are needed.

A standard and commonly used method of detecting target nucleic acids involves the use of oligonucleotides as hybridization probes in the field of chemistry, molecular biology and biotechnology. Oligonucleotide probes are synthesized to have sequences that are complementary to the target DNA or RNA strands, enabling the probes to hybridize to the target DNA or RNA strands under suitably stringent conditions. The standard procedure requires the DNA or RNA target strands to be immobilized on a solid surface, membrane, or bead. Then an oligonucleotide probe, labeled with a reporter group for identification, is added and binds non-covalently to any region of the target DNA or RNA strand encoding a complementary sequence to that of the probe. Next, any residual, unbound oligonucleotide probe is washed away from the immobilized target oligonucleotide, and the presence of any bound probe is detected by means of an attached reporter group. Common reporter groups include radioactive atoms (phosphorus, iodine, sulfur, carbon, or tritium), fluorescent or chemiluminescent groups, and enzymes that generate colored or fluorescent products. Many variations on this procedure exist which are known to those skilled in the art, including use of sandwich hybridization complexes, and in situ hybridization methodologies.

One limitation in using the standard hybridization method for detecting target nucleic acids is non-specific binding of the oligonucleotide probes to the target DNA or RNA. Short oligonucleotides (e.g., 6-12 mers) are much more effective at detecting single nucleotide mismatches than longer ones, but have a lower affinity to the template than longer oligonucleotides. Gryaznov and Letsinger developed a method of increasing the selectivity of the nucleic acid probe to the target nucleic acids, by using two or more shorter oligonucleotide probes instead of a single, long oligonucleotide probe. (Gryaznov, et al. *Nucleic Acids Research*, 22: 2366-2369, 1994; Letsinger et al., U.S. Pat. No. 5,681,943) The two or more shorter oligonucleotide probes would have either an electrophilic group (for example, bromoacetido, tosyl) or a nucleophilic group (for example, phosphorothioate monoester) at their termini. These shorter oligonucleotide probes contain base sequences that would bind to adjacent positions on a complementary template. When the probes align along the template, the oligonucleotide probes are brought into proximity of one another and spontaneously ligate and form an irreversible covalent bond. The oligonucleotide probes spontaneously ligate without any additional activating agents or enzymes.

Despite this improvement to the standard hybridization method, false positives may still result from the oligonucleotide probes non-selectively binding to proteins or the solid support. Standard hybridization methods using static labeling groups are further limited in that they usually have to be performed on solid supports under stringent conditions and require careful washing (static labeling here refers to labels, such as fluorescent labels, that do not change their signal). In particular, when standard oligonucleotide probes are used to detect or image nucleic acids in fixed cells, the cells have to be carefully prepared and the conditions properly manipulated to avoid nonspecific signals. Typically, cells are first fixed, permeabilized and crosslinked with formaldehyde and/or ethanol using procedures that are known to those skilled in the art. Next, hybridization is carried out, followed by several careful washes to remove unbound probes. Thus, standard hybridization methods using statically labeled oligonucleotides require time for preparation of the cells, increase the likelihood of error, and cannot be used in live cells, where washing away unbound probes is not possible.

In recent years, new methods for detecting nucleic acids that involve a change in fluorescence intensity or emission wavelength have been developed. Fluorescence changing methods of detecting nucleic acids have several advantages, including that the unbound probe molecules can easily be distinguished from those bound to the desired target without the need of a washing step, and the methods can be used either in solution or on solid supports. Most importantly, they could be applied in intact cells because no washing is needed. Moreover, fluorescence changing methods that rely on simple intensity variation by changes in quenching have the further advantage of freeing more spectral ranges so that simultaneous probing of multiple analytes can be achieved.

The most well-developed quenching-based approach to nucleic acid detection is that of "molecular beacons," which consist of hairpin-forming DNAs labeled in the stem with a fluorophore and a quencher. The hairpin-forming DNA probe binds to a complementary sequence resulting in the hairpin opening and the quencher moving away from the fluorophore. These molecular beacons can be used in solution or in solid-supported approaches. However, this method is limited because the fluorescence change clearly depends on solution conditions, e.g. temperature, ionic strength, and thus conditions must be monitored carefully. Another disadvantage is that molecular beacon method is not as sequence selective as other DNA-sensing methods such as enzymatic approaches or some non-enzymatic autoligation methods. When the molecular beacon approach was recently used to image RNA in live mammalian cells, the results were disputed because these probes can give false positives by being degraded or by binding a protein instead of RNA. In fact, one beacon is known that binds a specific protein and lights up Fang, X.; et al., Anal. Chem. 72: 3280-3285 (2000)). There are many DNA- and RNA-binding proteins in a cell, so false positives are likely due to nonspecific binding of the probes.

The use of multicolored hairpin-shaped oligonucleotide probes (molecular beacons) was suggested for discriminating alleles (S. Tyagi et al., Nature Biotechnology 16: 49-53, 1998). The hairpin probes were reported as having significantly enhanced specificity as compared to linear probes. However, the reported specificity is not as high as phosphorothioate-iodide autoligation probes. As described above, such beacons suffer from false positives by binding proteins.

In early work, the preparation of nucleoside S-alkyl phosphorothioates was offered in 1969 (A. F. Cook, J. Am. Chem. Soc. 92(1): 190-195, 1969). The phosphorothioate group has a higher nucleophilicity than does the oxygen analog. Reactions with various halogen compounds was described. Intermolecular nucleophilic reactions of thymidine 3'-phosphorothioates were suggested in 1971 (S. Chladek and J. Nagyvary, J. Am. Chem. Soc. 94(6): 2079-2085, 1971). Dinucleotides and trinucleotides containing P-S-C 5' linkages were formed. Those reactions were not performed with oligonucleotides, nor were they used in the detection of DNAs or RNAs, nor did they contemplate fluorescent labels or quenchers.

U.S. Pat. Nos. 5,476,925, 5,646,260, 5,648,480 and 5,932,718 suggested the preparation and use of oligonucleotides having particular internucleoside linkages. The oligonucleotides are purported to have improved hybridization properties as compared to conventional oligonucleotides.

Coupling of oligonucleotides via displacement of a 5'-O-tosyl group by a 3'-phosphorothioate was suggested by Herrlein et al. (J. Am. Chem. Soc. 117: 10151-10152, 1995). The approach was illustrated by three different systems: ligation of a nicked dumbbell oligonucleotide, cyclization of a conjugate possessing a short oligonucleotide overlap at the juncture site, and closure of a cap at the end of a duplex. Herrlein et al. do not contemplate iodides or other leaving groups such as quenching leaving groups, and they do not use the coupling to detect DNA or RNA sequences.

The displacement of an α-haloacyl group by a phosphorothioate group is suggested as a non-enzymatic method of joining two oligonucleotides by U.S. Pat. No. 5,476,930. The two oligonucleotides are brought into close proximity by binding at adjacent positions on a target polynucleotide. No quenching leaving groups were suggested.

The use of 5'-iodonucleosides was shown to allow efficient non-enzymatic ligation of single-stranded and duplex DNAs (Y. Xu and E. T. Kool, Tetrahedron Lett. 38(32): 5595-5598, 1997). An iodothymidine phosphoramidite enabled the placement of a 5'-iodide into oligonucleotides. Quenching leaving groups were not suggested in this publication.

There still exists a need for a simple method for detection and imaging of nucleic acids that is fast and accurate. Additionally, methods that are not dependent on washing away of unbound probes would be desirable, especially methods that can be used in living cells and that have specificity for as little as single nucleotide differences in sequence.

Recently, Sando and Kool published on the internet a description of the use of a quencher as a leaving group in solution and on solid phase beads (J. Am. Chem. Soc. 124(10): 2096-2097, 2002; placed on the internet on Feb. 13, 2002).

SUMMARY OF INVENTION

Oligonucleotides containing a fluorophore and a specialized quencher that also acts as a leaving group are disclosed. Nucleophilic attack on the quenched DNA, causing release of the quencher group, results in a ligated molecule that is now fluorescent due to the absence of the quencher group. The oligonucleotides are useful in enzyme-free nucleic acid hybridizations and in the detection of wild type and mutant nucleic acid sequences.

BRIEF DESCRIPTION OF DRAWINGS

The following figures form part of the present specification and are included to further demonstrate certain aspects of the present invention. The invention may be better understood by reference to one or more of these figures in combination with the detailed description of specific embodiments presented herein.

BRIEF DESCRIPTION OF SEQUENCES

The following sequence listings form part of the present specification and are included to further demonstrate certain aspects of the present invention. The invention may be better understood by reference to one or more of these sequences in combination with the detailed description of specific embodiments presented herein.

SEQ ID NO:1 is 13mer: 5'-TGT*GGGCAAGAG-3'.

SEQ ID NO:2 is Wild type 50mer target sequence.

SEQ ID NO:3 is Mutant transversion 50mer target sequence.

SEQ ID NO:4 is 7mer MUT probe.

SEQ ID NO:5 is 16S rRNA sites 310-314 in ATCC1177 strain.

SEQ ID NO:6 is 16S rRNA sites 310-314 in MG1655 strain.

DETAILED DESCRIPTION

The invention is generally directed towards compositions and methods for the ligation of molecules and the detection thereof. The compositions and methods can be used in both in vitro and in vivo applications. Generally, a molecule contains a fluorophore, and a 5' quenching leaving group. Upon ligation with another molecule in intermolecular fashion, or with itself in intramolecular fashion, the quenching leaving group is displaced, and the fluorophore is no longer quenched. The change in fluorescent properties of the molecule can be detected, providing a quantitative and qualitative assay of ligation.

In one embodiment of the invention, the molecule containing the fluorophore and the quenching leaving group can be any type of molecule. For example, the molecule can be an organic compound, an organometallic compound, a nucleic acid, a peptide, a protein, a lipid, a carbohydrate, or other types of molecules.

When the molecule having a quenching leaving group and a fluorophore further contains a nucleophilic group, intramolecular displacement of the leaving group can result in creation of a circular molecule. This method can be used to prepare circular nucleic acid molecules, for example. This method can further be used to prepare circular peptides, and circular or crosslinked proteins.

The molecule having the quenching leaving group and a fluorophore can be a separate molecule from the molecule having a nucleophilic group. These first and second molecules can be the same type of molecules (e.g. nucleic acid, peptide, protein, organic, organometallic), or can be different types of molecules. The first and second molecules can be in solution, or one can be immobilized on a support.

Figure 1:
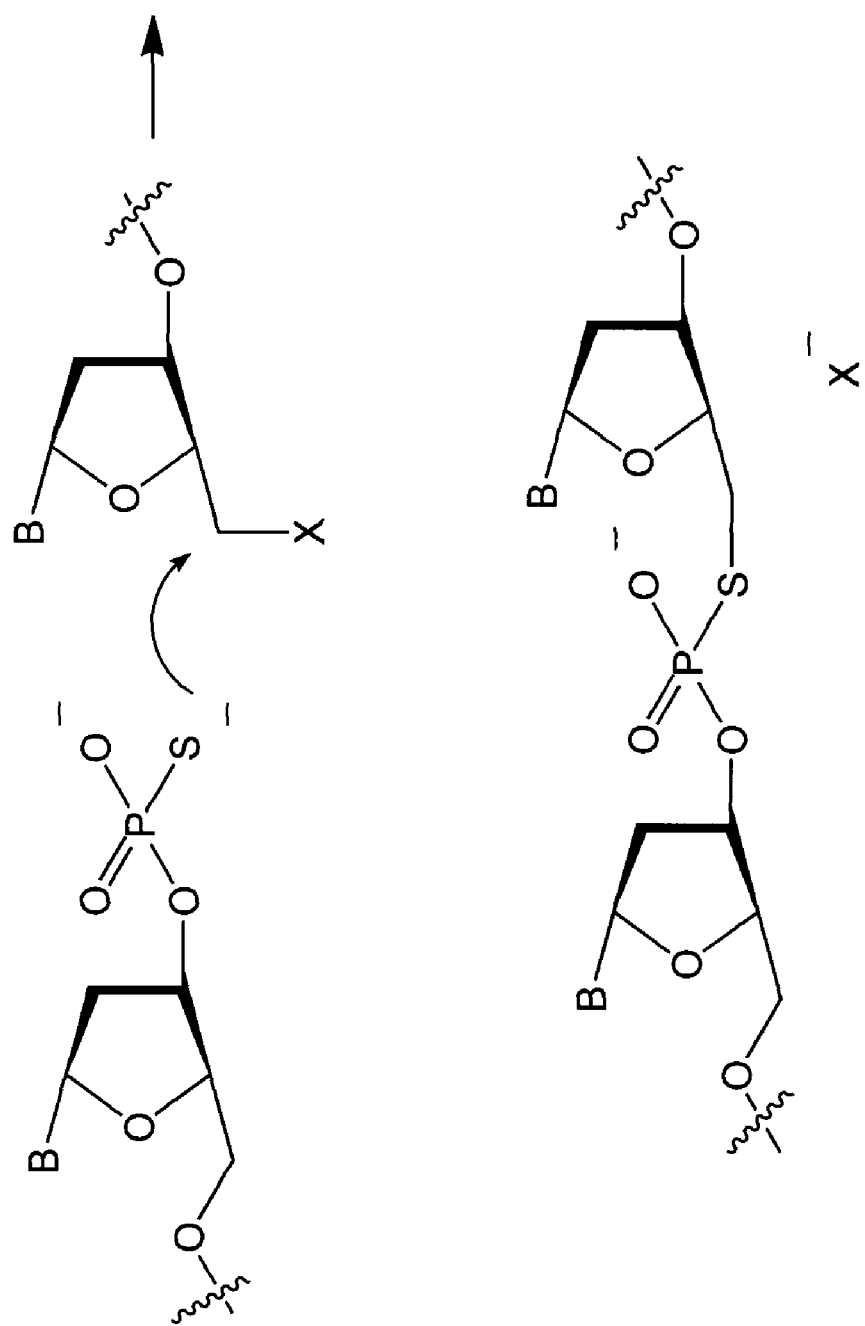
FIG. 1 shows the detection of a DNA sequence of interest using two nucleic acid probes that undergo chemical self-ligation by reacting a nucleophile on one probe with a carbon on another probe containing a leaving group (X).
Figure 2:
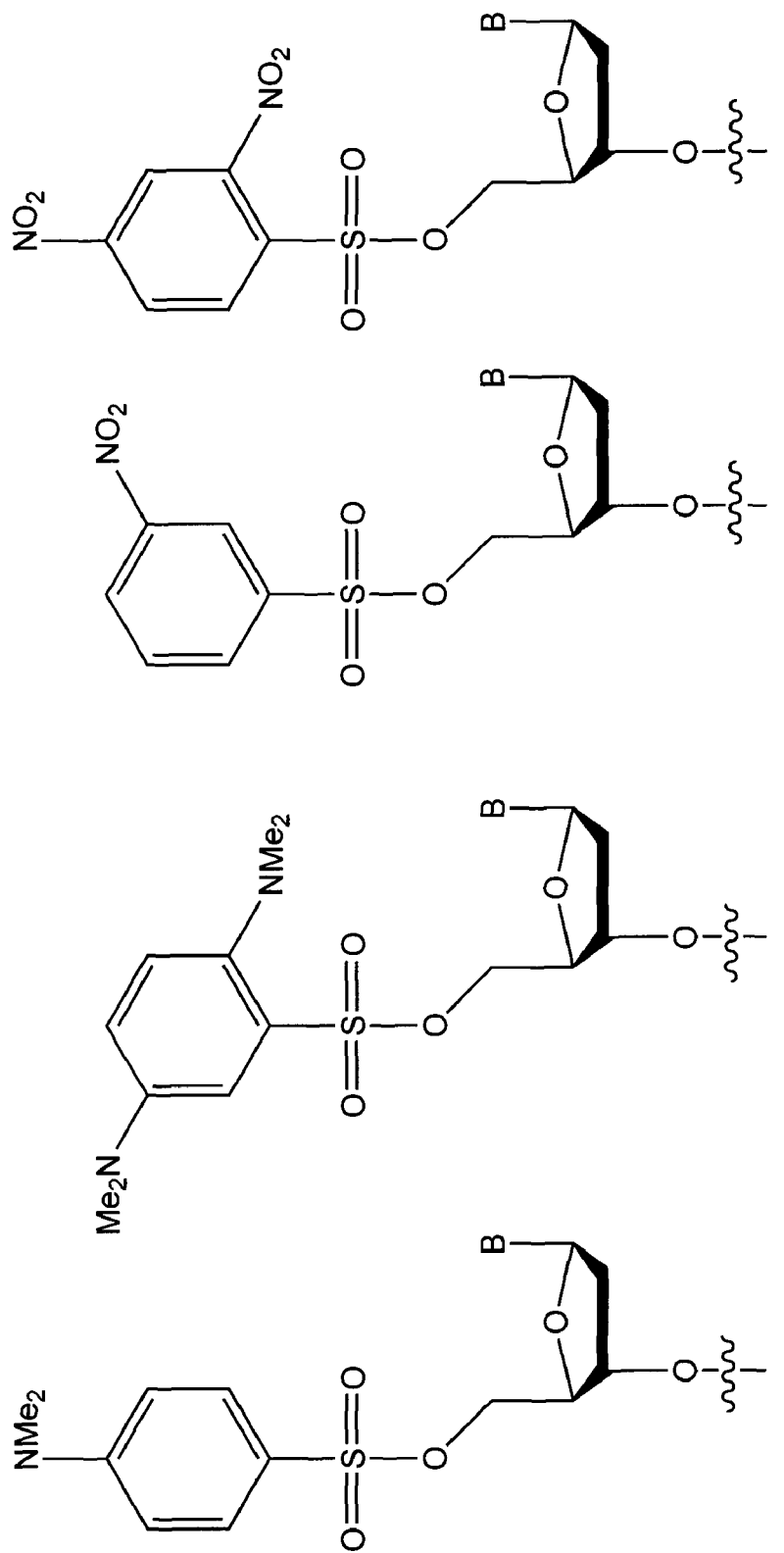
FIG. 2 shows four fluorescence quenching leaving groups attached to a nucleic acid molecule. Structure 1 shows a p-dimethylaniline-sulfonyl leaving group, structure 2 shows a tetramethyl-phenylenediamine-sulfonyl leaving group, structure 3 shows a nitrobenzene-sulfonyl leaving group, and structure 4 shows a dinitrobenzene-sulfonyl leaving group.

Examples of quenching leaving groups are shown in FIG. 2 (note that in the figure they are attached to the 5' carbon of a nucleoside, but they can be attached to any atom that is reactive with a nucleophile. The leaving groups in the figure include the sulfur and the three oxygen atoms attached to it, as well as the carbon chain attached to sulfur. Leaving groups in general are defined by (a) their ability to activate an atom (to which they are attached) for attack by a nucleophile group and (b) to leave (either simultaneously or subsequently) when the nucleophile does attack.

In general, nucleophilic groups (contemplated in this Invention) include phosphorothioate and phosphoroselenoate groups, thiol and thiolate groups, hydroxy and oxyanion groups, amines, hydroxylamines, hydrazines, hydrazides, phosphines, thioacids and their conjugate bases, selenols and selenoates. These can be attached to any molecule or object.

Embodiments of the invention can be performed in solution in the presence of complementary RNAs or DNAs. The two nucleic acid molecules preferably encode for adjacent sites along the complementary RNA or DNA. This brings the reactive ends of the two nucleic acid molecules into close proximity. In the intramolecular case, one reactive end binds adjacent to the other reactive end.

Embodiments of the invention provide multiple advantages over the prior art. It offers a smaller spectral window, thus making background fluorescence less problematic, and allowing for a greater number of simultaneous detection events using multiple colors. Additionally, the result is viewable to the naked eye. The result is simple to interpret, as probes remain dark unless they find the correct target, in which case they "light up" under fluorescence excitation. Another advantage is low probability of false positive signals as a result of undesired protein binding. The inventive compositions and methods do not require extensive washing or preparation steps.

An embodiment of the invention is directed towards a quencher labeled nucleic acid molecule. The nucleic acid molecule can generally be any type of nucleic acid molecule such as DNA, RNA, 2'-O-methyl-RNA, phosphorothioate DNA, locked nucleic acid ("LNA"), or PNA. A presently preferred nucleic acid molecule is DNA or 2'-O-methyl-RNA. The quenching group is preferably covalently attached to the 5' hydroxyl group of the nucleic acid molecule. The nucleic acid molecule can generally be single stranded or double stranded. It is presently preferred that the nucleic acid molecule is single stranded. The nucleic acid molecule can generally be any length of nucleotide bases (or base pairs if double stranded) in length. For example, the length can be about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 30, about 40, about 50 bases, about 60 bases, about 70 bases, about 80 bases, about 90 bases, about 100 bases, or any length range between any two of these lengths.

Generally any nucleophilic group can be used to displace the quenching leaving group. For example, the nucleophile can be a phosphorothioate, phosphoroselenoate, or other known nucleophilic groups. The nucleophile can located at the 5' end, 3' end, or between the 5' and 3' ends in a nucleic acid probe. In other types of molecules, the nucleophile can be located at any position.

Generally any fluorescence quencher can be used. The quencher can be a dabsyl (dimethylamino-azobenzene-sulfonyl) group, a dimapdabsyl ((p-dimethylamino-phenylazo) azobenzenesulfonyl) group, other azobenzene-sulfonyl groups, benzenesulfonyl groups with other substituents such as amino, dialkylamino, nitro, fluoro, and cyano groups, and other arenesulfonyl groups containing these substituents. Also contemplated are gold particles conjugated to sulfonyl leaving groups. The dabsyl activated 5' hydroxyl group is the leaving group upon attack by a nucleophilic moiety present on the second nucleic acid molecule (or other nucleophilic molecule). For example, a second nucleic acid molecule having a 3'-phosphorothioate can displace the 5' dabsylate group in forming a covalent bond between the two nucleic acid molecules. Alternatively, the 3' hydroxyl can be attached to a quenching leaving group. Any nucleoside, nucleotide, oligonucleotide, polynucleotide, natural or synthetic, can generally be modified to contain a quenching leaving group. For example, a dabsylthymidine derivative can be incorporated as the 5' terminus of the first nucleic acid molecule. Additionally, dabsyl can be added to the 5' terminus of an already isolated or synthesized DNA or RNA containing any natural or synthetic nucleotide at the 5' terminus. Dabsyl can also be added to hydroxyl groups on peptides; for example, on the hydroxyl groups of serine or threonine, or the sulfur group of a cysteine, or on a hydroxyl group formed when the carboxy group of an amino acid is reduced. The fluorescence quenching leaving group can also be on carbons of modified nucleic acids or nucleosides, such as on the 6' carbon of homo-dT, homo-dA, homo-dG, or homo-dC.

Dabsyl has long been used as a fluorescence quencher. However it has never before been used as a leaving group. It has previously been attached to amines, where it cannot act as a leaving group. It is the ability to act as a leaving group that allows embodiments of this invention to be successful: it causes the nucleophile to attack, and then it leaves, causing fluorescence to increase.

Generally any fluorophore can be used. Example fluorophores include fluorescein, TAMRA, Cy3, Cy5, Cy5.5, BODIPY fluorophores, ROX, JOE, and Oregon Green. An example incorporation of fluorescein is the use of fluorescein C-5-alkenyl conjugate of dU. Any known method of incorporating a fluorophore into a nucleic acid molecule can be used. It is prepared that the fluorophore be located close to the quencher, but this is not required. The fluorophore can generally be located at any distance from the quencher sufficient to permit detection of ligation by monitoring the change in fluorescent properties. For example, the fluorophore can be located 1, 2, or 3 nucleotides away from the quencher labeled nucleotide. The efficiency of quenching (i.e. the unquenched fluorescence with the fluorescence quenching group absent divided by the quenched fluorescence with the fluorescence quenching group present) is preferably at least about 2 fold, at least about 3 fold, at least about 4 fold, at least about 5 fold, at least about 10 fold, at least about 20 fold, at least about 30 fold, at least about 40 fold, at least about 50 fold, at least about 60 fold, at least about 70 fold, at least about 80 fold, at least about 90 fold, at least about 100 fold, at least about 200 fold, at least about 300 fold, at least about 400 fold, at least about 500 fold, at least about 600 fold, at least about 700 fold, at least about 800 fold, at least about 900 fold, at least about 1000 fold, at least about 2000 fold, at least about 3000 fold, at least about 4000 fold, or at least about 5000 fold.

The produced increase in fluorescence can generally be detected by any method. For example, fluorescence can be detected visually, with a fluorescence microscope, with a fluorescence spectrometer, or with a fluorescence microplate reader. Additionally, the fluorescence can be monitored using flow cytometric methods.

The above described molecules containing fluorophores and quenching leaving groups can be used in solution, on surfaces, in immobilized cells, or in living cells. The cells can generally be any type of cells, such as bacterial cells, plant cells, yeast cells, mammalian cells, CHO cells, human cells, cancer cells, fixed cells, virus infected cells, yeast cells, zebrafish cells, and nematode cells.

The above described molecules containing fluorophores and quenching leaving groups can be provided in lyophilized state or in solution or affixed to a solid support. For example, oligonucleotides can be affixed to a solid support. The oligonucleotides can be provided as part of a kit designed to detect a particular wild type or mutant sequence in a target nucleic acid sequence. The kit can comprise control target sequences, instructions, protocols, buffers, cells, and other common biological components.

The above described nucleic acid molecules can be used in methods to detect the presence or absence of particular mutations within a population of cells. Additionally, the nucleic acid molecules can be used in methods to detect the presence or absence of a particular type of cells by designing the nucleic acid molecules to bind to a unique nucleic acid sequence. For example, a method for the detection of an undesired bacteria or other harmful microbe could be designed where oligonucleotide ligation would occur (thereby causing fluorescence) only in the presence of the undesired or pathogenic microbes or viruses in a sample. A vast array of such microbes and viruses exist. Examples include *Mycobacterium tuberculosis, Mycobacterium avium, Mycobacterium intracellulare, Bordatella pertussis, Neisseria gonorrhea, Neisseria meningitdis, Escherichia coil* 0157:H7, and *Bacillus anthracis*.

The above described nucleic acid molecules can be used to detect a particular genetic sequence in solution, in a fixed cell, in an intact cell, in a part of an organism (e.g. a tissue sample), or in an intact organism. The molecules can be used to detect gene expression and to discriminate and identify differences in cells.

An additional embodiment of the invention involves the use of multiple differently-colored probes to simultaneously detect multiple nucleic acid sequences. This could be used to discriminate and identify different types of cells, normal cells from diseased cells (e.g. cancerous cells or virus infected cells), or multiple DNAs or RNAs in a cell.

The above described molecules and methods can be used to monitor changes in gene expression in cells over time, or in response to exposure to a drug, drug candidate, or other therapeutic agents.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Reaction in Solution

Wild type and mutant sequences 50 nucleotides in length were chosen from the H-ras gene. A known C to A transversion in codon 12 was selected to fall at the center of a 7mer binding site. The nucleophilic 7mer sequence was 5'-CCGTCGG-3' (SEQ ID NO:4), where the central T hybridizes to the A transversion, but not to the wild type C. The nucleophilic sequence contained a 3' phosphorothioate group. The electrophilic 13mer sequence was 5'-TGT*GGGCAAGAG-3' (SEQ ID NO: 1). A dabsyl group was used on the 5' hydroxyl as a leaving group of the electrophilic sequence, and a commercially available fluorescein C-5-alkenyl conjugate of dU (marked as T*) was used to place the fluorophore two nucleotides away from the quencher. The wild type target sequence was 3'-ATATTCGACCACCACCACCCGCGGCCGCCACACCCGTTC TCACGCGACTG-5' (SEQ ID NO:2), and the mutant transversion target sequence was 3'-ATATTCGACCACCAC-CACCCGCGGCAGCCACACCCGTTC TCACGC-GACTG-5' (SEQ ID NO:3; where the C to A transversion is underlined).

Gel electrophoresis was used to monitor the reaction. PAGE showed ligated product when the target sequence was fully complimentary to the two oligonucleotides, and no product when there was a single nucleotide mismatch. Conversion after 7 hours was estimated to be about 80% when the sequences were fully complementary. The starting materials were only weakly fluorescent due to incomplete quenching by the dabsyl group, while the product was strongly fluorescent.

The same reaction was monitored in real time by following fluorescence emission at 520 nm (with excitation at 495 nm). The change in fluorescein emission showed about a 100 fold increase in intensity, implying a 99% quenching efficiency for the starting molecule). Varying the temperature from 15° C. to 37° C. showed that the reaction rate reached a maximum near 25° C., which is the approximate melting temperature of the two probes bound to the target. The sequence selectivity was approximately 35-fold based on the relative peak areas with the wild type and mutant target sequences, resulting in a T-A pair or a T-C mismatch at the mutation site.

Example 2

Reaction on a Solid Support

As many genetic analysis methods use probes affixed to beads, slides, and other surfaces, a solid support was used to evaluate the instant invention. A 7mer MUT probe (5'-CCGTCGG-3'; SEQ ID NO:4) on 90 μm beads (1000A pore size) using commercially available reverse (5'→3') phosphoramidites was used, placing a 3' phosphorothioate moiety on the final 3' hydroxyl group. A hexaethylene glycol linker was used to alleviate potential crowding problems near the polymer surface. Such beads then have the potential to autoligate a 13mer quenched electrophile probe to themselves, in the presence of the correct target DNA. This was expected to result in the beads becoming fluorescent, as the dabsylate group was lost and the nearby fluorescein label lost quenching. The solid-phase autoligations were monitored by imaging under a fluorescence microscope. Results showed that the reaction proceeded on the polystyrene beads much as it does in solution. At the start of the reaction, the beads were dark and the solution showed only faint green fluorescence due to a small amount of emission from the quenched 13mer probe. As the reaction proceeded the beads became progressively brighter, reaching half-maximum after about 20 hours. Although the reaction rate appears to be slower on this solid support, using a different nucleophile, such as selenium, is likely to improve this. Moreover, it seems possible that increased linker length may lessen surface effects that hinder reaction. Finally, in many applications, it will be unlikely that the reactions need to be carried out to completion.

Example 3

Use of TAMRA as a Fluorophore

Example 1 was repeated using a different fluorophore. The use of different fluorophores would make it possible to sense multiple genetic sequences simultaneously. Dabsyl has been reported as a quencher for varied fluorophores. The same ligations on beads were carried out using a dabsyl/TAMRA electrophilic probe. The results showed that ligation and unquenching was also successful for the new dye.

Example 4

Staining of RNA in Fixed Cells

Next, the QUAL probes were used to stain RNAs in cellular specimens (for example, bacterial cells). There is a good deal of literature published in the last 3-4 years on using fluorescent oligonucleotides to stain 16S ribosomal RNAs in fixed bacterial specimens. These specific stains have been investigated for use in strain identification by microscopy and by flow cytometry (FCM). Targeting ribosomal RNAs allows one to identify bacterial genus and species and even substrains. Fortunately there is now a good deal of sequence information available for bacterial rRNAs, especially for *E. coli* strains. A further advantage of targeting ribosomal RNA is that its targetable secondary structure has been mapped. In addition, it exists in large copy number (there are many as 30,000 ribosomes in one cell), which is important in generating visible signal, since the bacterial cells are three orders of magnitude smaller than mammalian cells.

The standard oligonucleotide probes used in the recent literature for rRNA targeting are about 30 nucleotides in length (note that those standard probes use only static fluorescence and thus must require careful washing and cannot be used in live cells.) Initial studies involved autoligation probes 18 and 20 nucleotides in length, targeted to directly adjacent sites near residue 900 in 16S RNA in the 11775T strain.

The QUAL electrophile probe carried fluorescein quenched and activated by dabsyl as described above. Two different nucleophilic probes were synthesized: one perfectly complementary to a published sequence (S800), which was expected to ligate itself to the QUAL probe, and a control (S300) complementary to a different site 500 nt distant on the rRNA. The bacteria was grown and fixed (formaldehyde crosslinked and denatured) on glass slides, and hybridized at 25° C. in 20 mM Tris-HCl pH 7.2, 0.9 M NaCl buffer. The slides were monitored over time under the microscope. No washing was done. The probe solution was relatively dark because of efficient quenching by dabsyl, and one expects that the bacterial rRNAs will simply light up, focusing the fluorescence where the specific target resides. This was, in fact, what was observed. Specific green signals were strongly visible in the presence of the matched nucleophilic probe, while the mismatched S300 probe generated no visible signal. The lack of signal in the control case establishes that the positive signal does not arise from a trivial mechanism such as degradation of the quenched probe. Additionally, the unlabeled "helper" oligonucleotides that were designed to bind nearby and minimize secondary structure improved the signal up to 50-fold depending on helper and target site.

Importantly, the autoligation signal was strong after only three hours' hybridization, despite the fact that the ligation takes longer to reach stoichiometrically high conversion when target and probes are present at equimolar amounts. This was attributed to (a) a large excess of probe over target and/or (b) a bright signal, due either to large amounts of RNA and possibly some occurrence of turnover.

Example 5

Staining of RNA in Non-Fixed Cells

As the quenched autoligation method does not require washing or added enzymes, the method was used to detect RNAs in intact (non-fixed, and potentially live) bacteria. To date, there are few, if any, public reports of imaging RNAs in live bacteria. Standard fluorescent probes could not be used in such an application because they generate signals whether bound or unbound, and thus require washing away of unbound probes. The QUAL probes were introduced into the cells using standard electroporation/transfection methodology. The cells were electroporated for 2 sec (*E. coli* Pulser (Bio-Rad)) in 10% glycerol in the presence of two probes at 0.2 and 0.6 μM each (QUAL electrophile probe+S800 fully complementary nucleophile probe, or QUAL probe plus S300 mismatched nucleophile probe). The bacteria were simply left in a hybridization solution at room temperature for 3 hours and then imaged under the microscope. Results showed that at three hours, there was an easily visible green signal, which was essentially the same as that using fixed bacteria. The control probe generated no similar signal.

Example 6

Genetic Imaging of RNA in Bacteria

Probes targeted to ribosomal RNAs in *E. coli* K12 strain MG1655 were designed. The sequences of the 16S RNAs (about 1540 nucleotides in length) are known in this strain. Four sites were chosen: 1) nt 181-215; 2) nt 298-335; 3) nt 320-356; and 4) 873-910. Four probe pairs were constructed with thioate nucleophile probes (each 18-20 nt in length) and dabsyl-substituted electrophile probes (each 17-20 nt in length). The electrophile probes were fluorescein-labeled at uracil as a commercial C5-alkenyl conjugate within 3-4 nucleotides of the dabsyl end group.

Cells were fixed with paraformaldehyde according to literature methods, and were incubated with probes. When using probe pair #4, a distinct green signal was observed after 18 hours incubation. Incubation with the dabsylate probe alone yielded little or no signal. Thioate probe #4 with electrophile probe #3 also yielded little or no signal. This indicates that adjacent targeting of the nucleophile and the electrophile probes is helpful for generation of signal, and that non-specific binding of the probes is insufficient to create signal. Also, the data indicates that reaction of the probe pairs without the assistance of a target sequence does not occur to a detectable amount under these conditions.

Testing of appropriately matched probe pairs at all four 16S rRNA sites revealed a significant signal in all cases. This strongly suggests that multiple secondary structures are targetable by this approach. The amount of signal does vary, indicating that secondary structure does influence the outcome.

Example 7

Staining of RNA in Intact (Non-Paraformaldehyde Fixed) Cells without Electroporation Standard fluorescent oligonucleotide probes require fixation and permeabilization of bacterial cells because they must be carefully washed after hybridization to allow for removal of unbound or nonspecifically bound probes. In the present approach there is no requirement for this washing; thus the possibility of targeting rRNAs in intact bacterial cells was evaluated. Complementary FAM-G and control TAM-T probes were incubated with live MG1655 *E. coli* cells at 37° C. in the presence of 0.01% SDS to aid in uptake. This dilute detergent solution is reported not to affect the viability of *E. coli*. No prior fixation and permeabilization steps were performed, and again, no post-washing steps were carried out. Images were acquired directly in the probe solution. The experimental details for dabsyl-mediated autoligation reactions on 16S rRNA in non-fixed *E. coli* cells (surfactant introduction) were as follows.

*E. coli* cells (MG1655 or ATCC11775) were grown at 37° C. in LB broth (DIFCO). When an optical density at 600 nm reached 0.5, the suspension was chilled on ice for 5 minutes, 0.5 mL aliquots were taken into 1.5 mL vials, and cells were harvested by centrifugation for 5 minutes at 10,000 rpm at 4° C. Supernatant was removed and cells were resuspended in 100 µL Hybridization buffer (20 mM Tris-HCl pH 7.2, 0.9 M NaCl, and 0.01% SDS). To the suspension were added 2 µL of 20 µM dabsyl-probe, 6 µL of 20 µM phosphorothioate probe, and 1 µL of 500 µM helper oligonucleotide. The mixture was incubated at room temperature for 3 hours. After incubation, the suspension was directly spotted on glass slide without any washing steps and was covered with micro cover slide. Fluorescence images were obtained through a fluorescence microscope (Nikon Eclipse E800 equipped with 100× objective Plan Fluor apo) with super high pressure mercury lamp (Nikon model HB-10103AF), using a SPOT RT digital camera and SPOT Advanced imaging software. Typical microscope setting is as follows. Fluorescein: ex. 460-500 nm; TAMRA: ex. 530-560 nm with ND filters 8. Typical digital camera settings are as follows. Fluorescein: exposure time Green 6 sec, binning 2×2, gain 1; TAMRA: exposure time Red 3.5 sec, binning 2×2, gain 2.

Distinct green signals were seen for the bacteria after 3 hours, as expected for the probe complementarity. No signal was seen in the control, where a singly mismatched probe pair was used. An overlay of white-light and fluorescence images revealed a bimodal distribution, in which approximately half of the cells are stained and half are not. Notably, literature reports of oligonucleotide/rRNA hybridization with fixation and analysis by flow cytometry also show such a bimodal response, with ~50-70% of cells yielding signals. Regardless of the origin of this, these experiments establish that intact, non-fixed bacterial cells can be stained at single nucleotide resolution.

To our knowledge this is the first use of in situ hybridization in a non-fixed microorganism. This approach makes rRNA-based bacterial identification much more straight-forward than has been previously possible, as the lack of requirement for pre-preparation and post-washes greatly speeds and simplifies the process. Moreover, QUAL probes yield much higher sequence specificity than standard fluorescent probes.

Example 8

Single-base Specificity in Identification of Cellular RNAs

Tests of two-color rRNA hybridizations in fixed *E. coil* preparations were performed. Standard fixation protocols were carried out, using paraformaldehyde crosslinking. However, in the current experiments no post-hybridization washes to remove unbound and nonspecifically bounds probes were used. Initial experiments showed that sites in 16S RNA could generate signal with QUAL probe pairs as the only added DNA. Some sites were apparently hindered by competing secondary structure, however; for example, site 305-335 is predicted to be blocked by three regions of duplex. In those cases, an unlabeled "helper" probe as described by Amann was added. Such helper oligodeoxynucleotides have been reported to assist hybridization of standard fluorescent probes in regions of strong secondary structure. With QUAL probes a 17mer helper designed to bind adjacent to the dabsyl probe was observed to increase signal markedly.

To test single nucleotide selectivity, probes were varied by one base and have differently colored labels to distinguish which of the two yielded signal. Experiments revealed that either the FAM- or TAMRA-labeled probes give clear signals if perfectly complementary to the target RNA. By contrast, a single nucleotide mismatch in a probe of the opposite label led to no observable signal under the same conditions. Experiments lacking the nucleophile probe showed little or no signal, indicating that signal did not arise from accidental protein binding or nonspecific RNA binding. Also yielding no signal were control experiments in which nucleophile and electrophile probe were complementary to non-adjacent sites in 16S RNA. Thus the data show that only completely complementary probes binding side-by-side on an RNA target yield a signal. Overall, the results demonstrate a clear example of single-nucleotide specificity in in situ hybridization.

The above experiments tested sequence specificity by varying probe sequence. To further test the sequence specificity, a different strain of *E. coli* (ATCC1177) was obtained, which the sequence database reported to have a single nucleotide difference in the 16S rRNA (5'-GCAAC (SEQ ID NO:5) at sites 310-314 compared to 5'-GCCAC (SEQ ID NO:6) in the previous MG1655 strain). Green and red quenched probes (FAM-G probecomplementary to the original MG1655strain sequence, TAM-T complementary to the ATCC1177 sequence) were prepared to probe the reported single nucleotide difference. Surprisingly, the mixed probes yielded a distinctly green signal even though the red probe was complementary to the reported rRNA sequence. To investigate this independently, total RNA was isolated from the cells, RT-PCR was performed using 16RNA-specific primers, and the resulting DNA was sequenced. The sequencing results showed clearly that the RNA contains a C at position 312, in contrast to the database listing of an "A" at that position. Thus the QUAL probes again demonstrated single nucleotide specificity, allowing the identification of a single nucleotide sequencing error in the database.

Experimental details for synthesis of fluorescein- or TAMRA-labeled 5'-dabsyl oligonucleotides. Pac-protected dA, iPr-Pac-protected dG, and acetyl-protected dC phosphoramidites for ULTRA MILD SYNTHESIS (Glen Research) were employed in synthesizing oligonucleotides containing a dabsyl group. The fluorescein label and TAMRA label was introduced with fluorescein-dT and TAMRA-dT phosphoramidite (Glen Research), respectively. Deprotection and cleavage from the CPG support was carried out by incubation in 0.05 M potassium carbonate in methanol for 12 hours at room temperature. Following incubation, oligonucleotides were purified by reverse-phase HPLC (Allotec BDS-C18 column, 250 mm, eluting with 0.1 M triethylammonium acetate pH 7.0/acetonitrile).

Bacterial strains. Two *E. coli* strains were used: MG1655 and ATCC11775. Complete sequences of seven rrs operons (rrs A-H) of *E. coli* MG1655 strain were obtained from the database (http://www.ncbi.nlm.nih.gov/cgi-bin/Entrez/chrom?gi=1 15&db=G). A mean sequence of seven rrs operons (rrs A-H) of ATCC11775 strain was taken from EMBL databank (X80725).

Cell fixation. *E. coli* cells (MG1655 or ATCC11775) were grown at 37° C. in LB broth (DIFCO). When an optical density at 600 nm reached 0.5, the suspension was chilled on ice for 5 minutes, 1.0 mL aliquots were taken into 1.5 mL vials, and cells were harvested by centrifugation for 5 minutes at 10,000 rpm. After centrifugation, supernatant was removed and cells were washed once with 1 mL PBS. To fix the *E. coli* cells, cells were resuspended in 1.0 mL 4% paraformaldehyde/PBS fixation solution (filter sterilized, pH 8.0 adjusted by 1N NaOH) and the mixture was left at room temperature for 1 hour. After fixation, the cells were centrifuged at 10,000 rpm for 5 minutes, the supernatant was removed, and washed with 1 mL PBS. After the final wash, the fixed cells were resuspended in 1.0 mL 50% ethanol, then were stored at 20° C.

Dabsyl-mediated autoligation reactions on 16S rRNA in paraformaldehyde-fixed *E. coli* cells. 100 µL aliquots of the fixed *E. coli* stock suspension were taken into 1.5 mL vials and the fixed cells were collected by centrifugation at 10,000 rpm for 5 minutes. The cells were washed once with 100 µL PBS, and were resuspended in 100 µL Hybridization buffer (20 mM Tris-HCl pH 7.2, 0.9 M NaCl, and 0.1% SDS). To the suspension were added 2 µL of 20 µM dabsyl-probe, 6 µL of 20 µM phosphorothioate probe, and 1 µL of 500 µM helper oligonucleotide. The mixture was incubated at 37° C. for 18 hours. After incubation, the suspension was directly spotted on glass slide without any washing steps and was covered with micro cover slide. Fluorescence images were obtained through a fluorescence microscope (Nikon Eclipse E800 equipped with 100× objective Plan Fluor apo) with super high pressure mercury lamp (Nikon model HB-10103AF), using a SPOT RT digital camera and SPOT Advanced imaging software. Typical microscope setting is as follows. Fluorescein: ex. 460-500 nm; TAMRA, ex. 530-560 nm with ND filters 4 and 8. Typical digital camera settings are as follows. Fluorescein: exposure time Green 4 sec, binning 2×2, gain 1; TAMRA: exposure time Red 5 sec, binning 2×2, gain 2.

Example 9

Use of Alternative Fluorescence Quenching Groups

Other quenching leaving groups can also used in place of dabsyl. The choice of quenching leaving group for a given application depends on its ability to quench the dye of interest that is also substituted on a given probe, and on the activating ability. Some leaving groups are less reactive than dabsyl, and the resulting autoligation reaction is slower by comparison, but probes containing it may have increased sequence selectivity. Some leaving groups are more reactive than dabsyl, and may be useful to increase autoligation rates when greater speed is desired.

Figure 3:
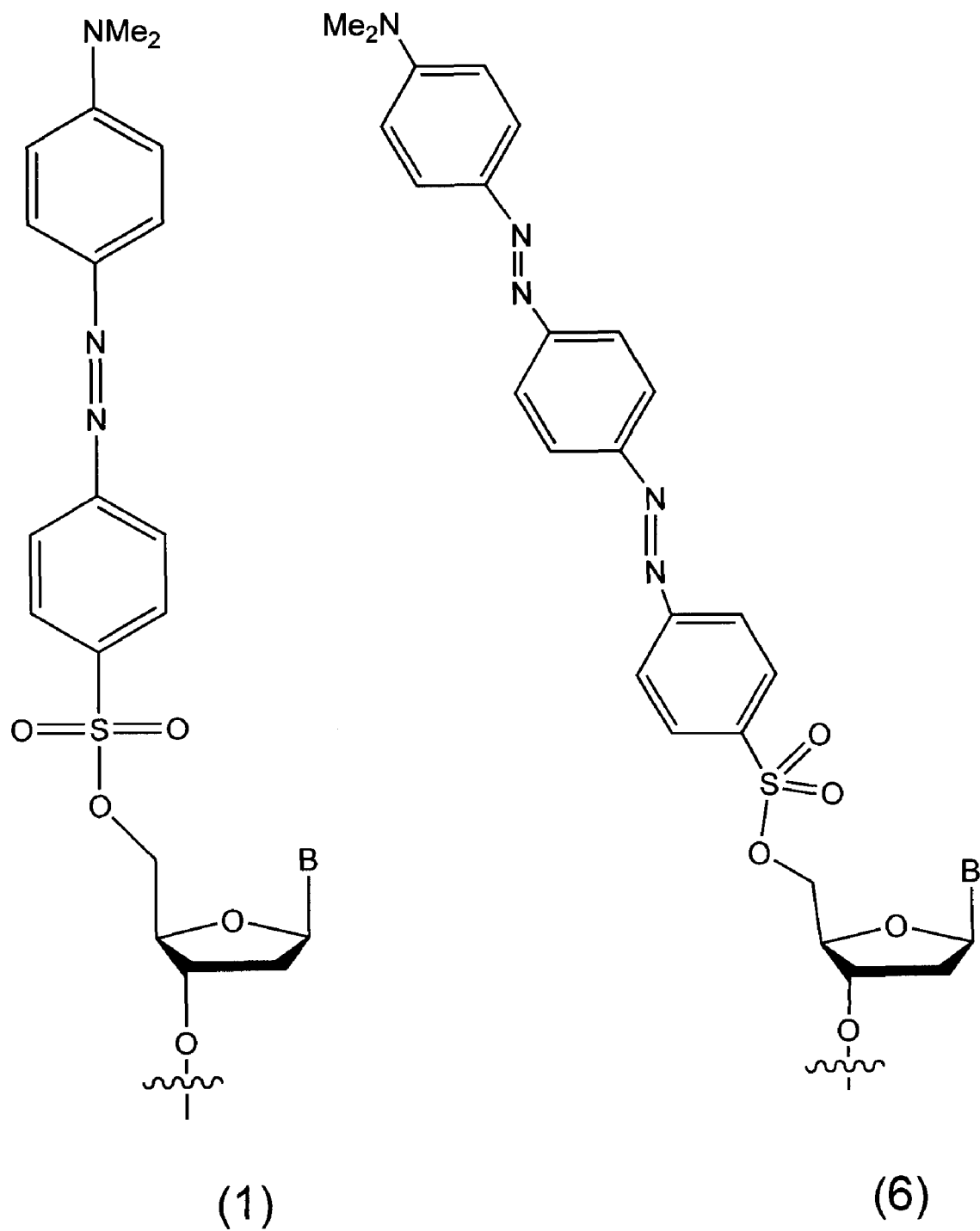
FIG. 3 shows two fluorescence quenching leaving groups attached to a nucleic acid molecule. Structure 5 shows a dabsyl leaving group, and structure 6 shows a (p-dimethylamino-phenylazo)azobenzenesulfonyl (DIMAPDABSYL) leaving group.

Examples of alternative quenching leaving groups are shown in FIGS. 2 and 3. In the structure shown the quenching leaving group is attached to a 5' hydroxyl group of DNA, but it is understood that attachment at other positions and in other types of molecules (e.g., peptides, proteins, carbohydrates) can also be done. In the example shown the 5' terminal base is given generically as "B", but it is understood that A, C, G, T, or U could also have been shown.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

The invention claimed is:

1. A composition comprising a fluorophore compound, the fluorophore compound comprising a fluorophore group and a fluorescence quenching leaving group, wherein said fluorescence quenching leaving group is a dabsyl group, a dimapdabsyl group, a p-dimethylaniline-sulfonyl leaving group, a tetramethyl-phenylenediamine-sulfonyl leaving group, a nitro benzenesulfonyl group, a dinitrobenzene-sulfonyl leaving group, wherein said fluorescence quenching leaving group contains a sulfur atom bonded to three oxygen atoms and a carbon chain.

2. The composition of claim 1, wherein the fluorophore compound is an organic compound, an organometallic compound, a nucleic acid, a peptide, a protein, a lipid, or a carbohydrate.

3. The composition of claim 1, wherein the fluorophore compound is a nucleic acid.

4. The composition of claim 3, wherein the nucleic acid is single stranded.

5. The composition of claim 3, wherein the nucleic acid is double stranded.

6. The composition of claim 3, wherein the quenching leaving group is attached to the 5' hydroxyl group of the nucleic acid.

7. The composition of claim 3, wherein the quenching leaving group is attached to a hydroxyl group other than the 5' hydroxyl group of the nucleic acid.

8. The composition of claim 3, wherein the fluorophore group is located 1, 2, or 3 nucleotides away from the quenching leaving group.

9. The composition of claim 1, wherein the fluorophore compound further comprises a nucleophilic group.

10. The composition of claim 9, wherein the nucleophilic group is a phosphorothioate or a phosphoroselenoate.

11. The composition of claim 1, wherein the fluorophore group is fluorescein, TAMRA, Cy3, Cy5, Cy5.5, BODIPY fluorophores, ROX, JOE, or Oregon Green.

12. The composition of claim 1, wherein the fluorophore compound is a peptide or a protein.

13. A method of detecting intramolecular chemical ligation, the method comprising:
providing a composition in accordance with claim 9;
maintaining the composition under conditions suitable for intramolecular chemical ligation without added enzymes; and
determining the fluorescence of the composition.

14. The method of claim 13, further comprising determining the fluorescence of the composition before the maintaining step, wherein detection of an increase in fluorescence compared to the fluorescence before the maintaining step indicates intramolecular chemical ligation.

15. The method of claim 13, wherein the intramolecular chemical ligation occurs at a greater rate in the presence of an analyte than in the absence of an analyte.

16. The method of claim 13, wherein the determining step comprises visual detection, detection with a fluorescence microscope, detection with a fluorescence spectrometer, detection with a flow cytometer, or detection with a fluorescence microplate reader.

17. A method of detecting intermolecular chemical ligation, the method comprising:
providing a first composition in accordance with claim 1;
providing a second composition comprising a nucleophile compound, wherein the nucleophile compound comprises a nucleophilic group;
combining the first composition and the second composition to form a reaction mixture without added enzymes; and
determining the fluorescence of the reaction mixture.

18. The method of claim 17, further comprising determining the fluorescence of the first composition before the combining step, wherein detection of an increase in fluorescence compared to the fluorescence before the combining step indicates intermolecular chemical ligation.

19. The method of claim 17, wherein intermolecular chemical ligation occurs between the fluorophore compound and the nucleophile compound at a greater rate in the presence of an analyte than in the absence of an analyte.

20. The method of claim 17, wherein the determining step comprises visual detection, detection with a fluorescence microscope, detection with a fluorescence spectrometer, detection with a flow cytometer, or detection with a fluorescence microplate reader.

21. A method of detecting a nucleic acid sequence of interest, the method comprising:
providing a nucleic acid molecule suspected of comprising a nucleic sequence of interest;
providing a first nucleic acid probe that hybridizes to at least a portion of the nucleic acid sequence of interest;
providing a second nucleic acid probe that hybridizes to at least a portion of the nucleic acid sequence of interest adjacent to the first nucleic acid probe;
combining the nucleic acid molecule, the first nucleic acid probe, and the second nucleic acid probe to form a mixture;
maintaining the mixture under conditions suitable for hybridization of the first nucleic acid probe and the second nucleic acid probe to the nucleic acid molecule without added enzymes; and
determining the fluorescence of the mixture; wherein:
the first nucleic acid probe is a composition in accordance with claim 1;
the second nucleic acid probe comprises a nucleophilic group; and
when the first nucleic acid probe and the second nucleic acid probe hybridize to the nucleic acid molecule, the nucleophilic group displaces the fluorescence quenching leaving group.

22. The method of claim 21, wherein the fluorescence quenching leaving group is covalently attached to the 5' end of the first nucleic acid probe, and the nucleophilic group is covalently attached to the 3' end of the second nucleic acid probe.

23. The method of claim 21, wherein the fluorescence quenching leaving group is covalently attached to the 3' end of the first nucleic acid probe, and the nucleophilic group is covalently attached to the 5' end of the second nucleic acid probe.

24. The method of claim 21, wherein the fluorescence quenching leaving group is covalently attached to the first nucleic acid probe one nucleotide away from the fluorophore group.

25. The method of claim 21, wherein the fluorescence quenching leaving group is covalently attached to the first nucleic acid probe two nucleotides away from the fluorophore group.

26. The method of claim 21, wherein the fluorescence quenching leaving group is covalently attached to the first nucleic acid probe three nucleotides away from the fluorophore group.

27. The method of claim 21, wherein the nucleic acid molecule is DNA.

28. The method of claim 21, wherein the first nucleic acid probe is DNA.

29. The method of claim 21, wherein the second nucleic acid probe is DNA.

30. The method of claim 21, wherein the nucleic acid molecule is RNA, 2'-O-methyl-RNA, phosphorothioate DNA, locked nucleic acid ("LNA"), or PNA.

31. The method of claim 21, wherein the first nucleic acid probe is RNA, 2'-O-methyl-RNA, phosphorothioate DNA, locked nucleic acid ("LNA"), or PNA.

32. The method of claim 21, wherein the second nucleic acid probe is RNA, 2'-O-methyl-RNA, phosphorothioate DNA, locked nucleic acid ("LNA"), or PNA.

33. The method of claim 21, further comprising the step of determining the fluorescence of the mixture prior to the maintaining step, wherein detection of an increase in fluorescence compared to the fluorescence prior to the maintaining step indicates presence of said nucleic acid sequence of interest.

34. The method of claim 21, wherein the determining step comprises visual detection, detection with a fluorescence microscope, detection with a fluorescence spectrometer, detection with a flow cytometer, or detection with a fluorescence microplate reader.

35. A kit for the detection of a nucleic acid sequence of interest, the kit comprising:
   a first nucleic acid probe that hybridizes to at least a portion of the nucleic acid sequence of interest; and
   a second nucleic acid probe that hybridizes to at least a portion of the nucleic acid sequence of interest adjacent to the first nucleic acid probe; wherein:
   the first nucleic acid probe comprises fluorophore group and a fluorescence quenching leaving group;
   the second nucleic acid probe comprises a nucleophilic group; and
   when the first nucleic acid probe and the second nucleic acid probe hybridize to a nucleic acid molecule comprising the nucleic acid sequence of interest, the nucleophilic group can displace the fluorescence quenching leaving group.

36. The kit of claim 35, wherein the fluorescence quenching leaving group is covalently attached to the 5' end of the first nucleic acid probe, and the nucleophilic group is covalently attached to the 3' end of the second nucleic acid probe.

37. The kit of claim 35, wherein the fluorescence quenching leaving group is covalently attached to the 3' end of the first nucleic acid probe, and the nucleophilic group is covalently attached to the 5' end of the second nucleic acid probe.

38. The kit of claim 35, wherein the fluorescence quenching leaving group is covalently attached to the first nucleic acid probe one nucleotide away from the fluorophore group.

39. The kit of claim 35, wherein the fluorescence quenching leaving group is covalently attached to the first nucleic acid probe two nucleotides away from the fluorophore group.

40. The kit of claim 35, wherein the fluorescence quenching leaving group is covalently attached to the first nucleic acid probe three nucleotides away from the fluorophore group.

41. The kit of claim 35, wherein the first nucleic acid probe is DNA.

42. The kit of claim 35, wherein the second nucleic acid probe is DNA.

43. The kit of claim 35, wherein the first nucleic acid probe is RNA, 2'-O-methyl-RNA, phosphorothioate DNA, locked nucleic acid ("LNA"), or PNA.

44. The kit of claim 35, wherein the second nucleic acid probe is RNA, 2'-O-methyl-RNA, phosphorothioate DNA, locked nucleic acid ("LNA"), or PNA.

45. The composition of claim 1, wherein said fluorescence quenching leaving group is a dabsyl group.

46. A probe pair comprising a first and second probe, wherein said first probe comprises a fluorophore group and a fluorescence quenching leaving group, said fluorescence quenching leaving group containing a sulfur atom bonded to three oxygen atoms and a carbon chain, and selected from the group consisting of a dabsyl group, a dimapdabsyl group, a p-dimethylaniline-sulfonyl leaving group, a tetramethyl-phenylenediamine-sulfonyl leaving group, a nitro benzenesulfonyl group, a dinitrobenzene-sulfonyl leaving group, wherein said second probe comprises a nucleophilic group.

47. The probe pair of claim 46, wherein said first probe is a dabsyl-substituted electrophile probe, and said second probe is a probe containing a nucleophilic phosphorothioate group.

* * * * *

UNITED STATES PATENT AND TRADEMARK OFFICE
CERTIFICATE OF CORRECTION

| | | |
|---|---|---|
| PATENT NO. | : 7,749,699 B2 | Page 1 of 1 |
| APPLICATION NO. | : 10/604400 | |
| DATED | : July 6, 2010 | |
| INVENTOR(S) | : Erik T. Kool | |

It is certified that error appears in the above-identified patent and that said Letters Patent is hereby corrected as shown below:

Replace Column 1, line no. 12-17 with:

-- FEDERALLY-SPONSORED RESEARCH OR DEVELOPMENT
This invention was made with Government support under contract DAAD19-00-1-0363 awarded by the U.S. Army Research Laboratory and contract GM062658 awarded by the National Institutes of Health. The Government has certain rights in this invention. --

Signed and Sealed this
First Day of January, 2013

David J. Kappos
*Director of the United States Patent and Trademark Office*